United States Patent [19]

Caisey et al.

[11] Patent Number: 5,725,600
[45] Date of Patent: *Mar. 10, 1998

[54] PROCESS FOR IMPROVING THE RESULTS OF COSMETIC TREATMENTS PERFORMED ON BLEACHED HAIR

[75] Inventors: Laurence Caisey, Vitry-sur-Seine; Christian Monnais, Neuilly-sur-Seine; Henri Samain, Bievres, all of France

[73] Assignee: L'Oreal, Paris, France

[*] Notice: The term of this patent shall not extend beyond the expiration date of Pat. No. 5,679,113.

[21] Appl. No.: 433,795

[22] Filed: May 3, 1995

[30] Foreign Application Priority Data

May 4, 1994 [FR] France .................. 94 05470
May 4, 1994 [FR] France .................. 94 05469
May 4, 1994 [FR] France .................. 94 05468

[51] Int. Cl.$^6$ ..................................... D06L 3/04
[52] U.S. Cl. ................... 8/103; 8/102; 8/405; 8/444; 8/115.52; 132/200; 132/203; 132/208
[58] Field of Search ................... 8/103, 102, 444, 8/115.52, 405, 137; 132/203, 208, 200

[56] References Cited

U.S. PATENT DOCUMENTS

| | | | |
|---|---|---|---|
| 3,281,263 | 10/1966 | Priesing et al. | 8/115.52 |
| 4,792,341 | 12/1988 | Kozikowski et al. | 8/103 |
| 5,246,019 | 9/1993 | Godfrey et al. | 8/409 |
| 5,303,722 | 4/1994 | Godfrey et al. | 132/219 |

FOREIGN PATENT DOCUMENTS

| | | |
|---|---|---|
| 3330293 | 3/1985 | Germany. |
| 9106279 | 5/1991 | WIPO. |
| 9410874 | 5/1994 | WIPO. |

*Primary Examiner*—Alan Diamond
*Attorney, Agent, or Firm*—Nixon & Vanderhye

[57] ABSTRACT

A process for improving the results of cosmetic treatments on bleached hair is provided.

9 Claims, 2 Drawing Sheets

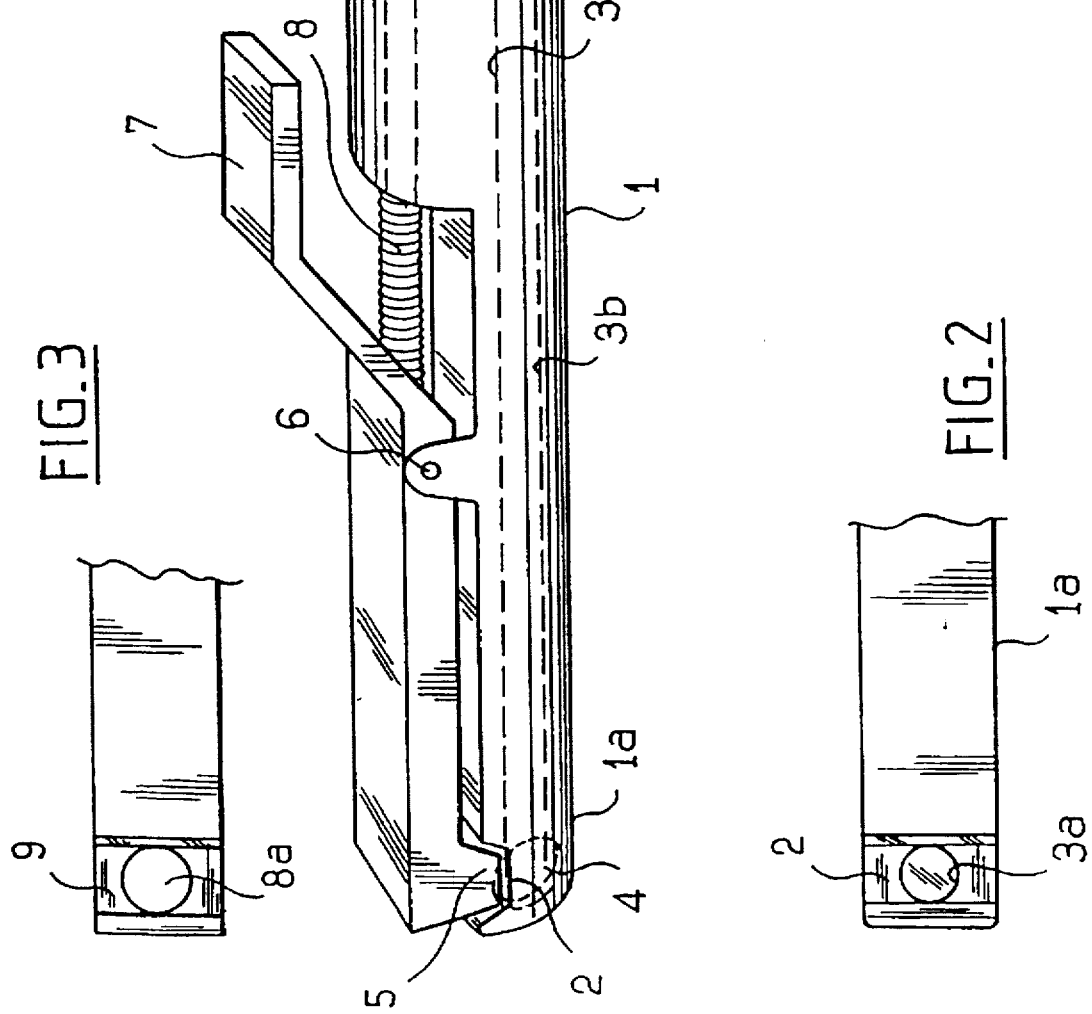

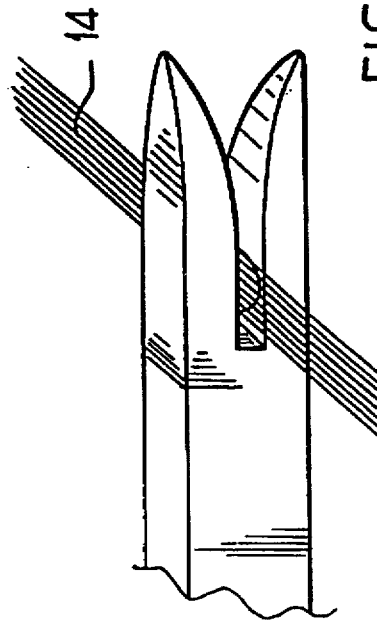
FIG._5
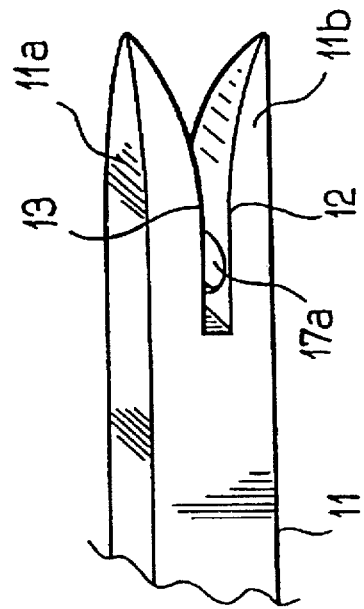
FIG._7
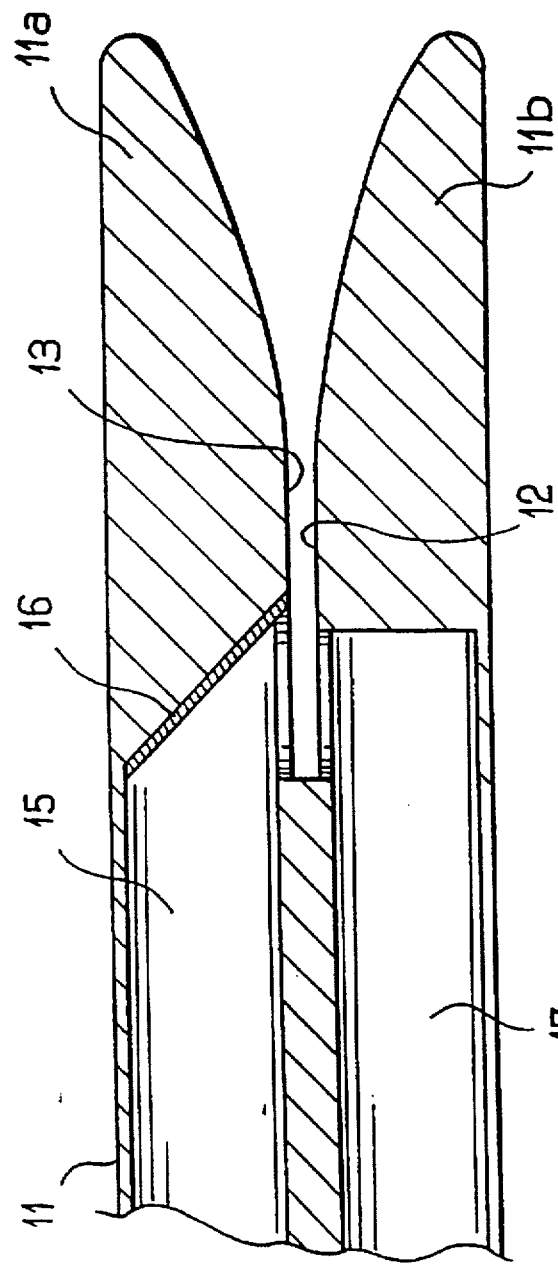
FIG._6

PROCESS FOR IMPROVING THE RESULTS OF COSMETIC TREATMENTS PERFORMED ON BLEACHED HAIR

The invention relates to a process for improving the results of cosmetic treatments performed on bleached hair. It has in fact been discovered that the results of cosmetic treatments performed on bleached hair were markedly improved when the said treatment is performed on hair bleached by irradiation with a laser beam.

It is known that, in order to bleach or lighten the colour of hair, it is conventional to use a chemical treatment with the aid of an oxidizing agent, such as hydrogen peroxide or persalts, which destroys at least part of the natural and/or artificial colouring substances present in the hair.

The conventional method of chemically bleaching hair requires the use of relatively powerful and/or concentrated oxidizing agents which have the effect of degrading not only the colouring substances but also the keratinous fibre of the hair. The result of this is that hair bleached in this way is fragile and must subsequently be treated with care.

For these reasons, it is difficult or sometimes impossible to obtain good results with the cosmetic treatments applied to hair bleached by chemical route.

For example, it is impossible for permanent-reshaping treatments used for natural hair to be applied to such bleached hair, since these treatments consist in applying, to the hair, reducing agents at relatively high pH values and then an oxidizing agent, these having markedly aggressive effects on the keratinous fibre of the hair. In fact, application of a conventional permanent-reshaping treatment on a bleached head of hair by chemical route causes irreversible degradation and even hair breakages.

This explains why experienced hairdressers do not undertake to perform a permanent-reshaping operation immediately or soon after bleaching by chemical route. In order to perform a permanent-wave treatment on hair which is rendered fragile in this way, they use "weak" permanent-wave compositions, that is to say those using markedly smaller doses of reducing agent and/or exhibiting a pH close to neutral. Under these conditions, the degradation of the hair is more limited. However, hair treated in this way exhibits an unattractive frizziness. The curls obtained do not have the elasticity of those obtained by the permanent reshaping of natural hair. Furthermore, when the hair has been highly bleached, it is possible that the permanent-wave treatment causes no curliness. It is recalled here that the operation of permanent reshaping of hair is commonly called a "permanent wave" and that the hair which has undergone such an operation is called "permed".

Moreover, it is known that a large proportion of people desire to have a so-called "highlighted" head of hair, that is to say a head of hair which has not been totally bleached but in which only certain locks of hair have been bleached. This involves a so-called "highlighting" operation. The case of highlighted heads of hair is particularly tricky since natural hair and highly bleached hair are then encountered on the same head of hair. The natural hair requires, in order to curl, a "strong" permanent-wave product, whereas, in order to limit the problems of degradation, only a "weak" permanent-wave product should be applied to the bleached hair. Since such a procedure cannot be used in practice, these difficulties are generally solved by coating the bleached locks using a protective substance and then a fairly strong permanent-wave composition is applied to the entire head of hair. With this technique, the natural hair is permed quite well, but the bleached locks are generally quite damaged and exhibit unattractive curls. Furthermore, this technique is lengthy since it requires having to coat each bleached lock with the protective substance. The final result is quite unsatisfactory since certain locks (the natural locks) curl well whereas other locks (the bleached locks) hardly curl at all.

In fact, in the case of practically all cosmetic treatments applied to bleached hair, difficulties of execution or disappointing results are observed.

It is known, for example, that certain people wish to obtain not only bleached locks but coloured locks having a shade different from that of the rest of the head of hair. In order to achieve this, the said locks should first be bleached and then a colouring agent applied to the head of hair. It turns out that the dyeing is not stable on the bleached locks. Moreover, with oxidation dyes, which develop coloration only in the presence of an oxidizing agent, the previously bleached locks are even further damaged since they are more sensitive to the inevitably degrading effect of the oxidation-dye treatments. Furthermore, certain dyes have difficulty in colouring previously bleached hair. In addition, the bleached and then dyed locks exhibit problems of dye fastness. Indeed, they tend to rapidly fade in colour by washing using a shampoo.

The application of hair-conditioning agents to bleached hair also leads to disappointing results since this hair is easily entangled and the application of conditioning agents, such as disentangling agents or mousses to be rinsed out, do not prevent breakage of bleached hair, when combing out, because they are fragile.

Likewise, after applying certain hair lacquers, bleached hair joined to unbleached hair by particles of lacquer may become torn out when combing.

Similar problems may be encountered after applying setting lotions. Furthermore, since bleached hair is softer than natural hair, the result of this is that the hairstyle does not have a uniform appearance, even after applying a lacquer or setting lotion, in particular when the head of hair is highlighted.

Moreover, the application of shampoos containing detergents is less well withstood by the keratinous fibres of bleached hair, in particular in the case of frequent shampoos. Thus, it may be seen that virtually all cosmetic treatments applied to bleached hair pose problems which are difficult or sometimes even impossible to solve.

The invention makes it possible to remedy these various drawbacks thanks to the discovery that it is possible to bleach hair by irradiation with laser radiation, and this is so without adversely affecting the mechanical and physico-chemical properties of the hair.

The invention therefore makes it possible to apply, with good results and without taking special precautions, the various usual cosmetic treatments, including those which have just been mentioned. These improved results are obtained by applying the said treatments to hair bleached not by chemical route but by irradiation using a laser beam, under special conditions which make it possible to achieve, on all types of hair, whether coloured naturally or artificially, bleaching of easily controllable intensity, without appreciable degradation of the keratinous fibre, and with a reasonable treatment time. This bleaching process is particularly well suited to obtaining a highlighted head of hair. Furthermore, the hair bleached in this way, having kept the mechanical and physico-chemical properties that it had before bleaching, may be subjected immediately to other cosmetic. treatments without it being necessary to use protective substances, and improved results are obtained for all the usual cosmetic treatments.

The theoretical possibility of bleaching hair with laser radiation was mentioned in the publication Tech. News, *Laser Focus*, Vol. 19, No. 9, p. 26, September 1983. Furthermore, in U.S. Pat. No. 4,792,341, an experimental device has been described which makes it possible to study the destruction of the melanin of the hair using laser radiation. In fact, this U.S. patent describes neither a process nor a device making it possible, in practice, to apply the laser irradiation to the bleaching of hair.

It has now been discovered that it is possible to bleach locks of hair whatever their original (natural or artificial) colour, without degradation of the keratinous fibre, by successively subjecting parts of the locks of hair to be treated to irradiation by a laser beam as long as a laser-radiation power is chosen which is suitable for the type of hair to be bleached.

Studies on isolated hairs of various origins (European, Japanese, Mexican and Scandinavian natural hair) have made it possible to study the luminous power necessary to obtain good bleaching of hair without degradation of the keratinous fibre, with a single laser pulse (one-shot firing). It has been observed that very dark (Japanese or Mexican) hair does not become sufficiently bleached in depth or shatters under the irradiation when the power per unit area is further increased, for a given pulse duration. By using a peak power less than the highest peak power which, in one-shot firing, for the pulse duration used and for the type of hair under study, does not cause shattering of the keratinous fibre, successive shots were subsequently carried out, in sequences, on the same area of the isolated hairs treated. It has been discovered that the isolated hairs, even very dark hairs of the Japanese or Mexican type, could be bleached without damage by lowering the peak power in this way and by carrying out several successive passes on a treated area, thereby making it possible to bleach firstly the surface layers and then the deeper layers, and eventually the hairs may be completely bleached.

Similar studies performed on locks of hair have enabled it to be established that it is possible to bleach hair arranged in locks, as long as a laser-radiation power suitable for the type of hair treated is selected. This power must be sufficient to degrade or destroy the melanin but must not exceed a certain threshold. It has been discovered that the darker the natural colour of hair, the lower this threshold has to be. This therefore leads to the surprising result that the more difficult the hair is to bleach, the more the laser-radiation power has to be moderated.

As will be obviously apparent to those skilled in the art, it is in fact the energy delivered to the particles of melanin, over a sufficiently short time duration, which has to be high enough to degrade or destroy the melanin. In reality, it is therefore the energy density delivered per unit area, in a sufficiently short time, which has to reach a threshold high enough for the hair to be able to be bleached. In the present application, when one speaks of "power" or "peak power", it should be understood that this is a language simplification as it is in fact the energy delivered during each pulse which is important, and it is therefore necessary to take into account the duration of the pulse which must be, however, not greater than approximately one microsecond (approximate duration of the relaxation time of melanin) in the case of the bleaching of natural hair.

It has also been discovered that it is possible similarly to bleach artificially coloured hair as long as the operation is performed, as for undyed hair, by adapting the power of the laser radiation to the natural colour of the hair. It is only after having performed this preliminary step, corresponding to the degradation of melanin, that the bleaching proper, corresponding to the degradation of the artificial dye, may be undertaken. In fact, the degradation of artificial dyes requires higher energies than the degradation of melanin, such that, if it is desired to degrade the said dyes directly, the hair would be destroyed by the shattering of the keratinous fibre, as in the experiments mentioned hereinabove.

Moreover, it is known that certain old people have a "white" head of hair which in fact has an unattractive yellowish tint. The laser irradiation bleaching process makes it possible to convert this yellowish coloration into pure white.

The subject of the invention is therefore a process for improving the results of cosmetic treatments performed on bleached hair, characterized in that the said treatment is performed on hair bleached by irradiation using laser radiation.

The subject of the invention is in particular a process as defined hereinabove, in which the hair to which the treatment is applied has been bleached by a process in which at least one lock or portion of lock is bleached, at least partially, by irradiation of the said lock or portion of lock using a laser beam of sufficient power to bleach the hair, this bleaching process comprising the following steps:

an area of the said portion of lock is treated by irradiation using a laser beam emitted in the form of pulses in order to bleach, at least partially, the hair in the said area, by degradation of the melanin in the hair, if required, by relative movement of the said lock with respect to the said laser beam, one or more other areas are treated in succession, in a similar way, so as to treat the totality of the said portion of lock, the above treatments are possibly repeated until the desired degree of bleaching is obtained for the said lock or portion of lock, the operation is performed with laser radiation of sufficient power to deliver, per pulse, an energy density of 0.1 to 1.2 $J/cm^2$ at 532 nm, the said chosen energy density not being greater than a threshold above which the keratinous fibre of the hair is damaged, the said threshold being lower the darker the natural colour of the hair to be treated.

It is known that a laser is essentially composed of an active medium rendered amplifying by a pumping mechanism delivering energy to the atoms in a selective way, the said active medium being contained in a resonant cavity. The active medium is then capable of emitting a substantially monochromatic, polarized and coherent light beam. Because of this coherence, a laser beam concentrates a markedly greater energy than that of radiation emitted by a conventional light source.

Certain lasers, especially those with a solid-state active medium, are capable of emitting laser radiation in the form of very short pulses (generally between one femtosecond and one microsecond). The concentration of energy into such short time intervals gives the laser pulse a considerable power, called peak power. In the process of the invention, lasers are preferably used which allow production of controlled pulses. For example, it is possible to use ruby lasers or lasers for which the active medium contains ions of rare earths or of actinides, for example a neodymium-type laser. The construction of such lasers is well known. The active ions may be inserted into a crystalline matrix, such as yttrium aluminium garnet (YAG for short), or into an amorphous matrix such as a glass. The pulse repetition frequency is adjusted using a pumping flashlamp. The available energy may be adjusted using conventional systems, especially polarizers.

Preferably, lasers are used which emit in the near ultraviolet, in the visible or in the near infrared, for example at wavelengths of 300 to 1100 nm. For example, it is possible to use a neodymium-YAG laser which emits at 1.06 µm, possibly with a frequency multiplier which makes it possible, for example, to obtain 532 nm wavelength emission (double the frequency) or 355 nm wavelength emission (three times the frequency).

The peak-power/pulse-duration pair (for example the peak power of the laser beam for a given pulse duration) may be easily determined by taking into account the conditions concerning the energy density per pulse, as a function of the natural colour of the hair, even if dyed hair is involved. More precisely, it is desirable not to exceed a maximum energy density per pulse which is of the order of:

0.35 J/cm² for very dark brown hair (of the Japanese or Mexican type),
0.4 J/cm² for dark chestnut hair,
0.5 J/cm² for light chestnut hair,
0.7 J/cm² for dark blond hair,
1.2 J/cm² for light blond hair.

The various data supplied hereinabove relating to the energy density were established for a radiation of 532 nm wavelength. When the wavelength used is different, a correction factor $\lambda_{nm}/532$ should be applied, as is explained in more detail in the experimental part hereinbelow.

Moreover, it is recalled that the various hair colours may be defined objectively using the luminance (L), according to the colorimetric (L,a,b) coordinate system of the C.I.E (Comité International de l'Eclairage [International Lighting Committee]). In the present application, the hair colours mentioned correspond to the luminance ranges mentioned hereinbelow:

|  | L |
|---|---|
| Japanese or Mexican | less than 18 |
| Dark chestnut | 18–20 |
| Light chestnut | 22–24 |
| Dark blond | 28–35 |
| Light blond | 45–52 |

The process described hereinabove, which corresponds to at least partial bleaching by degradation of the melanin in the hair, must be performed, in all cases, even if hair dyed using a colouring agent is treated and, in this latter case, the bleaching process comprises an additional step of irradiation of the hair, similar to the step described hereinabove, but by laser radiation delivering a higher energy density, sufficient to destroy or degrade the colouring agent; this energy density is especially at least equal to 0.8 J/cm². It is generally less than 2 J/cm² at 532 nm.

In order to implement the preliminary step of degradation of the melanin, all that is required is to know the natural colour of the dyed hair to be treated and then irradiation conditions are applied which are suitable for the hair having this natural colour, the said conditions having been determined beforehand, once and for all, by simple routine experiments.

The duration of the pulses may range, for example, from 10 picoseconds to 100 nanoseconds.

The laser bleaching process obviously requires bleaching the head of hair in locks, by successively irradiating areas of the said lock. Generally, the irradiation area may vary within the range 0.1–2 cm².

This process is therefore particularly well suited for obtaining highlighted heads of hair. In order to treat the areas to be bleached in succession, by relative movement of a lock with respect to the laser beam, it is possible to move the lock with respect to the apparatus used for the treatment, or vice versa, and/or to vary the direction of the laser beam periodically so as to perform successive scans of the treated area. This periodic variation in the direction of the laser beam may be achieved, for example, using an oscillating mirror.

It has been observed that, when bleaching is performed by laser shots in sequence, the hair tends to heat up locally. In order for this local heating not to be able to damage the hair, it is advisable to limit the pulse repetition frequency and/or to carry out sufficient relative movements of the treated lock of hair with respect to the laser beam so as to prevent cumulative heating, after which it is possible to return to a previously treated area, having had time to cool down sufficiently, in order to complete the treatment, and so on. Another solution for preventing local heating of the hair is to cool the hair in the treated area. It is especially possible to cool the hair in the treated area by circulating a fluid. The simplest solution is to create a gas flow bathing the hair in the treated area, for example by sucking in the air or even by blowing a gas, possibly cooled beforehand, such as air, nitrogen, helium, carbon dioxide, etc. Of course, it is possible to use a gas laden with water vapour or laden with liquid particles (aerosol), for example water droplets.

In practice, it is easy to determine a suitable pulse repetition frequency and/or an appropriate speed of movement of the lock of hair with respect to the laser beam simply by routine experiments, the said suitable frequency and/or the said appropriate speed being those for which heating potentially damaging to the hair is not observed. For example, it is possible to choose a pulse repetition frequency which can range from 5 to 50 Hz. The method, consisting in periodically varying the direction of the laser beam, as indicated hereinabove, also constitutes one of the means of combating the local heating of the hair. In the case in which measures are taken to cool the hair, it is possible to operate with pulse repetition frequencies greater than those which have just been indicated. In this case, the pulse frequency may range, for example, up to 1000 Hz, especially from 10 to 100 Hz approximately. The capacity of the cooling system to remove the heat produced, so as to prevent thermal degradation of the hair, must obviously be adapted to the choice of the pulse frequency, which itself conditions the duration of the treatment.

The treated hair may be dry or wet.

In order to be able to bleach the treated lock of hair under good conditions, it is preferable to arrange this lock in the form of a ribbon of hair and it is then possible to bleach the hair in the treated area by irradiating at least one of the faces of the said ribbon. Preferably, the thickness of the ribbon of hair corresponds to the thickness of approximately 3 to 20 superposed hairs.

According to a particular embodiment, the bleaching step of the laser bleaching process is characterized in that:

the operation is performed using a treatment device which includes a receptacle for the lock of hair to be treated, the surface of the said receptacle having an orifice for the exit of the said laser beam, the hair of the said lock, spread out in the form of a ribbon, is applied, over at least part of its length, to the surface of the said receptacle so that an area to be treated is opposite the said orifice, irradiation of the said area is then carried out, and, by relative movements of the said lock with respect to the laser beam, irradiation of the other areas to be treated is carried out in succession.

Devices allowing such an implementation will be described hereinbelow. With these devices, the relative movements of the lock with respect to the laser beam may be achieved by relative movements of the lock with respect to the said receptacle and/or by periodic variations in the direction of the laser beam, as indicated previously.

One of the advantages of the bleaching of hair by irradiation with a laser beam is that it is possible to monitor continuously the bleaching produced and to stop the treatment at the chosen degree of bleaching.

As indicated hereinabove, the main advantage of laser irradiation bleaching is that the hair is not degraded and the mechanical and physico-chemical properties that it had before treatment are preserved. Here there is a considerable advantage since it is possible to perform, on the hair bleached in this way, other treatments having a degrading effect without necessarily observing a minimum delay time between the two operations and without taking special precautions. Thus, it is possible to give hair bleached by irradiation with a laser beam a permanent wave either immediately or shortly after bleaching. It is not necessary to take special measures to protect the bleached locks before applying the permanent-wave composition. It is possible, and even desirable, to use permanent-wave compositions at normal dosing levels, for natural hair, which makes it possible to obtain good results both for bleached locks and for the rest of the head of hair.

The invention therefore makes it possible especially to implement a process for the permanent waving of bleached hair, characterized in that the permanent-reshaping treatment of the hair is performed, according to the known methods, on hair bleached by irradiation with a laser beam.

In order to implement the hair-bleaching step defined previously, it is possible to use a device which includes:

a body equipped with a receptacle, the said receptacle being intended to serve as a housing, over at least part of the length of the hair, for a lock of hair to be treated, the lock being spread out in the form of a ribbon;

means intended to convey a laser beam so as to irradiate at least one area of a lock of hair arranged in the said receptacle;

and, if required, means for cooling the said hair in the irradiation area or areas.

In particular embodiments, this device may also have the following characteristics, taken in isolation or, if required, in combination:

the said receptacle includes a wide-bottomed groove, making it possible to spread out the said ribbon on the said bottom;

the said groove may be associated with a disengageable piece of cooperating shape, capable of being inserted into the said groove, leaving, between the said piece and the bottom of the groove, a space forming a housing for the said ribbon; the said piece be disengaged, for example, by actuating a lever which makes it possible to introduce the lock to be treated into the receptacle or to remove it therefrom; the bottom of the said groove and/or one face of the said piece opposite the said bottom may have an orifice for the exit of a laser beam onto the area to be irradiated; likewise, the bottom of the said groove or one face of the said piece opposite the said bottom may have an orifice for creating a gas flow (by sucking or blowing);

in another embodiment, the said receptacle includes a groove in the form of a narrow slot emerging at the surface of the said body and having a depth sufficient to allow insertion of the said ribbon over the totality of its width; in a way similar to that mentioned hereinabove for the first embodiment, at least one of the faces opposite the said narrow slot may comprise an orifice for the exit of a laser beam; and at least one of the faces opposite the said narrow slot may comprise an orifice for creating a gas flow.

Finally, it should be noted that the laser channel and the conduit for creating a gas flow may be coincident.

Of course, the receptacle must form a light-tight confined space in order to prevent the laser radiation from causing damage to the user or to his clients.

The subject of the present invention is also the use of the bleaching of hair using laser radiation in order to improve the processes of cosmetic treatments performed on bleached hair.

By using the process which has just been described in detail, it is possible to perform, on hair bleached in this way, and under good conditions, various cosmetic treatments necessary for hair care. These treatments are especially the execution of a permanent-reshaping operation, a colouring operation or a shampooing operation, or else the application of a lacquer, a conditioning composition, a setting lotion, etc.

The technical cosmetic-treatment processes whose results may be improved by means of the process of the invention are known per se. The case of the permanent reshaping of hair is recalled hereinbelow by way of illustration.

The step of permanent reshaping of hair which has been bleached by the process indicated hereinabove may be performed using the standard methods, this not being possible, as recalled hereinabove, when the hair has been bleached by chemical route. The permanent-reshaping operation may be performed immediately after bleaching or a few days or a few weeks later.

It is recalled that the permanent reshaping of hair is carried out in the standard way using a two-step process which consists, firstly, in treating the hair with a reducing agent in order to open the disulphide bonds of the keratin in the hair, and then, after preferably having rinsed the head of hair, in applying, to the mechanically tensioned hair, an oxidizing composition (so-called setting step) so as to reconstitute the said disulphide bonds and thus to give the hair the desired shape. This technique makes it possible both to give the hair waviness and to straighten it or to uncrimp it.

The reducing and oxidizing compositions which can be used in the processes for permanently reshaping hair are well known and described especially in the cosmetology literature. The reducing agent is, for example, thioglycolic acid, thiolactic acid, or an alkaline or ammonium sulphite or bisulphite.

The tensioning of the hair is performed for example, in a known way, by rolling it on hair-curlers. In the case of straightening, the tensioning of the hair is achieved, for example, by smoothing out the hair with a comb.

The oxidizing agent is especially hydrogen peroxide or a persalt.

The invention will now be described with reference to the appended drawings in which:

BRIEF DESCRIPTION OF THE DRAWINGS

FIG. 1 is a diagrammatic view of a first embodiment of the device of the invention, which includes, at its end, a receptacle in the form of a wide-bottomed groove and a cooperating piece which can be actuated by a lever;

FIG. 2 is a partial view from above of the end, carrying the receptacle, of the device of FIG. 1;

FIG. 3 is a partial view from below of the end of the said cooperating piece of the device of FIG. 1;

FIG. 4 illustrates diagrammatically the mode of use of the device of FIG. 1;

FIG. 5 represents a diagrammatic sectional view of a second embodiment of the device, with a receptacle in the form of a narrow slot;

FIG. 6 is a vertical longitudinal sectional view of the device of FIG. 5;

and FIG. 7 shows diagrammatically the mode of use of the device of FIG. 5.

FIG. 1 shows that the device includes a partially hollow elongate body (1) whose front end (1a) of smaller cross-section comprises a receptacle having the shape of a flat-bottomed groove (2). A conduit (3) for the laser beam emerges in the bottom of the groove (2) after being sharply reflected by means of the mirror (4), and forms an exit window (3a) at the surface of the wall (2). The dotted lines (3b) show diagrammatically the propagation of the laser beam inside the body (1) or may represent a waveguide.

A cooperating piece (5), which can move about the axis (6), is held engaged in the receptacle by means of return means, such as a tension spring (not depicted), and can be disengaged by actuating the lever (7) with which the piece (5) is equipped at its rear end. A flexible tube (8) is connected to a compressed-air supply (not represented) and emerges in the face (9), opposite the bottom of the groove, of the piece (5) via an orifice (8a). The rear part of the body (1) serves as a handle for the apparatus to be gripped by the operator. In order to bleach the hair, the piece (5) is disengaged in order to be able to arrange the lock of hair (10), distributed in the form of a ribbon as indicated in FIG. 4, and then the piece (5) is allowed to re-engage in the groove. The lock therefore lies arranged in the space between the faces (2) and (9), the laser emitter (not represented) as well as the cooling system are actuated and the device is moved with respect to the lock (or vice versa) in order to bleach, in succession, the entire lock or portion of lock to be treated. It is preferable to perform movements which are not too slow, for example of the order of 0.1–5 centimeters per second and to do this in successive passes, thereby making it possible to monitor very easily the progress of the bleaching, under good safety conditions. However, it is also possible, with effective cooling, to use slower speeds of movement or discontinuous movements.

The body of the device my be made of any appropriate material, for example of light metal such as aluminium of plastic. The tubing (8) is a conventional flexible tubing. It may be connected to a suction system instead of the compressed-air supply.

The device represented in FIGS. 5 and 6 comprises an elongate body (11) of which only the front part has been represented, the rear part, not represented, forming the handle. It may be seen that the end of the body (11) splits into two branches (11a) and (11b) separated by a slot whose opposite faces (12) and (13) constitute a housing for a lock of hair (14) arranged as indicated in FIG. 7. As in the first embodiment, a laser channel (15) emerges on the face (13) of the slot, after having been reflected by the mirror (16), and a channel (17) connected to a compressed-air supply emerges at the surface of the wall (12) at (17a).

This device is used in a similar way to the previous one. The units for controlling the laser beam and the cooling circuit, which may be coupled, can be installed on the device or in a separate control unit which may possibly be foot-actuated. It is also possible to provide devices for slaving the laser power as a function of the colour of the lock to be treated, it being possible for this slaving to be carried out automatically after the colour has been read by an appropriate detector.

The following examples illustrate the invention.

EXAMPLE 1

In this example and in the following examples, 0.25 g locks of hair, having a length of 20 cm, are used.

The apparatus used is an apparatus of the type represented in FIG. 1.

The laser radiation source is a Surelite Continuum laser: wavelength 532 nm; shot frequency 1 Hz; beam diameter 5 mm; pulse duration 4 ns.

With this equipment, the ranges of optimal bleaching, depending on the colour of the hair to be treated, have been studied.

The ranges of energy per $cm^2$ for one pulse are those which can he used for bleaching hair effectively.

Below the minimum value, there is no appreciable bleaching. Above the maximum value, the fibre of an individual hair shatters or cracks up (the damage is visible, depending on its size, with a binocular magnifier, a microscope or an electron microscope).

The results are summarized in Table (I) below:

TABLE (I)

| Hair | energy/$cm^2$ for 1 pulse (in $J/cm^2$) |
|---|---|
| Japanese | 0.2 to 0.35 |
| Dark chestnut | 0.2 to 0.4 |
| Light chestnut | 0.15 to 0.5 |
| Dark blond | 0.15 to 0.7 |
| Light blond | 0.1 to 1.2 |

Moreover, the absorption of luminous energy by melanin varies with the wavelength—it decreases when the wavelength increases, in such a way that the hair withstands, without degradation, a higher incident energy density when the wavelength increases. The experimental study has shown that the maximum energy density which can be withstood by the hair, without the keratinous fibre shattering, for radiation of wavelength λ, is substantially that indicated in the above table, multiplied by a factor $$\lambda/532$$

where λ is expressed in nanometers. This law of variation with wavelength is also valid for the relationship between the incident energy density and the efficiency of the bleaching—the energy density capable of bleaching hair of a given type, for the wavelength λ, is substantially equal to the energy density enabling similar bleaching to be achieved with radiation of 532 nm wavelength, multiplied by the said factor $$\lambda/532$$

For artificially coloured hair, it is necessary to use quite high energy densities, generally at least equal to 0.8 $J/cm^2$ per pulse. If the hair has been coloured without prior bleaching, its natural colour must be taken into account. For example, if the natural colour of the hair was light chestnut, it is necessary firstly to use an energy density not greater than 0.5 a/$cm^2$ (see Table 1 above) in order to bleach the melanin. It is only afterwards that it will be possible to use a higher energy density (1 J/cm² or more) in order to destroy the artificial dye. If this high energy density were to be applied at the outset, the hair would shatter.

EXAMPLE 2

The procedure is as in Example 1, but with a Spectra-Physics Lasers Quanta Ray laser: wavelength 532 nm; shot frequency 50 Hz; beam diameter 8 mm; pulse duration 7 ns.

Cooling is provided by an airflow of 0.5 liter per second.

With this apparatus, the peak power per unit area, corresponding to optimum bleaching for dark chestnut hair, is of the order of 40 MW/cm², i.e. an energy per unit area of 0.3 J/cm².

EXAMPLE 3

The procedure is as above, but with a BMI laser having the following characteristics: wavelength 523 nm; shot frequency 20 Hz; beam diameter 3 mm; pulse duration 30 ps; helium-flux cooling.

Optimum bleaching of dark chestnut hair was achieved with an energy per unit area of 0.28 J/cm².

If the operation is performed by cutting off the flow of helium, degradation of the hair, with fusion of scales, visible with a magnifier or a microscope, is observed.

EXAMPLE 4

With the equipment described in Example 1, 0.2 g locks of hair, 20 cm in length, have been bleached by moving the bleaching tongs slowly along the lock.

Air cooling: flow rate 0.25 liters per second.

Pulse frequency: 10 Hz.

With dark chestnut hair and a pass of the totality of the lock taking approximately 5 minutes, complete bleaching was obtained after 5 passes using a peak power corresponding to an energy of 0.35 J/cm² per pulse.

For light blond hair, complete bleaching was obtained after a single pass lasting approximately one minute.

With dark chestnut hair, measurements were made of the alkaline solubility on natural hair, hair bleached by laser radiation and hair bleached by chemical route (hydrogen peroxide).

The alkaline solubility serves to characterize the state of degradation of the hair. The locks are immersed for 30 minutes at 65° C. in a 0.1N solution of sodium hydroxide, then rinsed 3 times by immersion for 5 minutes in distilled water and finally oven-dried at 105° C. until reaching a constant weight. The weight loss of the hair, in %, represents the alkaline solubility.

A determination was also made of the cysteic acid. After a hot hydrolysis treatment of the hair in acid medium, the quantity of cysteic acid passed into solution is measured, by separating out the amino acids on an ion-exchange resin and by performing a colour reaction using ninhydrin. On natural hair, the amount of cysteic acid is between 0 and 0.8%, on degraded hair, this amount increases.

It has been observed that laser bleaching leaves the alkaline solubility or the cysteic-acid content virtually unaltered, whereas these are greatly increased after bleaching by chemical route.

EXAMPLE 5

Four locks of 0.25 g of natural European hair, having a length of 20 cm, are taken. Lock No. 1 is subjected to three bleaching operations (Formulation No. 1) of 30 minutes.

Formulation No. 1

60 g of the following formulation:
oxyethylenated nonylphenol (4 EO) 25 g
oxyethylenated nonylphenol (9 EO) 20 g
oxyethylenated lauric acid (2 EO) 7 g
oleic acid 30 g
propylene glycol 12 g
1-hydroxy-4-(phenylemino)anthraquinone 0.05 g
ammonia solution (20%) 7 g
demineralized water q.s. for 100 g
mixed with 50 g of the following powder:
sodium persulphate 30 g
potassium persulphate 25 g
anhydrous sodium silicate 3 g
colloidal silica 0.4 g
ammonium-chloride 12 g
1-hydroxy-4-(phenylamino)anthraquinone 0.3 g
and furthermore mixed with 120 ml of the following solution:
30 volumes hydrogen peroxide* 100 g
phosphoric acid q.s. for pH 3
* 2.7 N aqueous solution of $H_2O_2$.

Lock No. 2 is subjected to bleaching by laser irradiation, in accordance with the invention, using the apparatus of the type represented in FIG. 1. The laser radiation source is a Surelite Continuum laser: wavelength 532 nm; shot frequency 1 Hz; beam diameter 5 mm; pulse duration 4 ns.

The two locks are lightened in colour to equivalent extents. (It was in order to obtain bleaching of lock No. 1 equivalent to that of lock No. 2 that it was necessary to treat lock No. 1 three times).

Both locks, and a third, unbleached, lock are wound on rollers of 9 mm in diameter, then the first permanent-waving lotion (Formulation No. 2) is applied and left on for 15 minutes. This is rinsed out and the second permanent-waving lotion (Formulation No. 3) is applied. This is left on for 5 minutes and then rinsed.

Formulation No. 2 thioglycolic acid 10 g ammonia solution q.s. pH 9 demineralizedwater q.s. 100 g

Formulation No. 3 hydrogen peroxide q.s. 8 volumes citric acid q.s. pH 3 demineralized water q.s. 100 g

Lock No. 4, not having been subjected to any treatment, serves as a reference.

The four-locks are washed and compared.

Curliness

Locks 2 and 3 exhibit good curliness. The first lock is virtually uncurled. The four wet and combed locks are hung up by one end. After a few minutes, locks 2 and 3 have a curled appearance. The curls are bouncy. The lower end of the hair has therefore risen. There is no rise in the first lock. After a few minutes, the height of the locks (distance from the root to the tip without stretching the lock) is measured.

| Locks: | height of the dry lock |
|---|---|
| 1. Chemical bleaching and then permanent waving | 30 cm |
| 2. Laser bleaching and then permanent waving | 22 cm |
| 3. Permanent waving | 22 cm |
| 4. Natural | 31 cm |

Locks No. 2, 3 and 4 have a pleasant and healthy feel. Lock No. 1 has an abnormal, slippery or "flaccid" feel.

EXAMPLE 6

A highlighting operation is performed on a head of hair of a European person. In order to do this, approximately 50 locks of 0.5 g are separated out and treated using the laser irradiation bleaching process in accordance with the invention.

Once the hair has been rinsed out, all the hair is rolled up on hair-curlers of 9 mm in diameter and a strong permanent-waving treatment (lotion 2 and then lotion 3, see Example 1) is carried out. The hair-curlers are removed and the hair rinsed. It is observed that the hair is uniformly curled. The bleached locks are just as curled as the natural locks. The feel of all the hair is good.

EXAMPLE 7

A highlighting operation is performed on a head of hair of a European person on numerous small locks, called "brush-stroking". In order to do this, using a comb, approximately 150 locks of 0.15 g are separated out for treatment using the laser irradiation bleaching process in accordance with the invention.

Once the hair has been rinsed out it is dried.

Two weeks later, all the hair is rolled up on hair-curlers of 9 mm in diameter and a strong permanent-waving treatment (lotion 2 and then lotion 3, of Example 1) is carried out. The hair-cutlers are removed and the hair rinsed out. It is observed that the hair is curled uniformly. The bleached locks are just as curled as the natural locks. The feel of all the hair is good.

EXAMPLE 8

Two locks of chestnut natural European hair and one lock of 70% grey natural European hair are taken. The first lock is subjected to three bleaching treatments (Formulation No. 1) of 30 minutes using hydrogen peroxide, persalts and ammonia solution.

The second lock is subjected to laser irradiation bleaching in accordance with the invention.

The first two locks are lightened in colour to equivalent extents.

The three locks are dyed with colouring, employing a mixture, weight by weight, of Formulations No. 4 and 5:

Formulation No. 4 para-phenylenediamine 0.1 g
meta-hydroxyphenol 0.3 g
meta-hydroxyphenol 0.1 g
meta-aminophenol 0.1 g
2-methyl-5-(β-hydroxyethyl)aminophenol 0.2 g
ammonia solution (20%) 10 g
ethyl alcohol 10 g
demineralized water q.s. 100 g Formulation No. 5

20 volumes hydrogen peroxide 100 g
phosphoric acid q.s. pH 2.5

It is observed that the first lock is very highly coloured. The shade is a coppery golden colour. The next two are moderately coloured and although the lock treated by laser irradiation and then by dyelug is a little darker than the natural lock treated by dyeing, the shades are very similar (coppery chestnut).

In addition, when the three locks are shampooed (6 shampooings), it is observed that the colour-fastness of locks 2 and 3 is very good. In contrast, the shade of the first lock is washed out, giving a yellow colour.

It is recalled that a so-called "20 volumes" hydrogen peroxide is a 1.8N aqueous solution of hydrogen peroxide.

EXAMPLE 9

Two locks of chestnut natural European hair and one lock of 70% grey natural European hair are taken. The first is subjected to three bleaching treatments (Formulation No. 1) of 30 minutes, employing hydrogen peroxide, persalts and ammonia solution.

The second lock is subjected to laser irradiation bleaching in accordance with the invention.

The first two locks are lightened in colour to equivalent extents.

The three locks are put in setting rollers.

The three locks are treated with a lacquer, employing an anionic copolymer (Formulation No. 6).

Formulation No. 6 methylvinylether/butyl maleate copolymer sold under the name "Gantrez ES425 L" (I.S.P.), 100% neutralized by aminomethylpropanol 5 g
ethyl alcohol q.s. 100 g
the formulation being pressurized by dimethyl ether (30 g for 100 g of formulation).

It is observed that locks 2 and 3 are softer and more easily disentangled than the first.

EXAMPLE 10

Two locks of chestnut natural European hair and one lock of 70% grey natural European hair are taken. The first is subjected to three bleaching treatments (Formulation No. 1) of 30 minutes, employing hydrogen peroxide, persalts and ammonia solution.

The second lock is subjected to laser irradiation bleaching in accordance with the invention.

The first two locks are lightened in colour to equivalent extents.

The three locks are subjected to a treatment of 8 shampooings (Formulation No. 7) (0.5 g of shampoo per gram of hair).

Formulation No. 7 polyoxyethylenated sodium lauryl ether sulphate (2.2 EO) in aqueous solution with 70% of active substance 15 g (AS)
lauryl betaine 2.5 g
demineralized water q.s. 100 g It is observed that locks 2 and 3 are softer and more easy to disentangle than the first.

EO means: ethylene oxide

AS means: active substance

We claim:

1. In a cosmetic hair treatment process comprising bleaching said hair and applying a cosmetic treatment to said bleached hair, the improvement which comprises irradiating said hair with a laser beam to achieve said bleaching, said irradiating comprising delivering an energy density per pulse of 0.1 to 1.2 J/cm$^2$ for a wavelength of 532 nm, said energy density not being greater than that which degrades the keratinous fibers of said hair, wherein the energy density is multiplied by a correction factor equal to $\lambda/532$ for a radiation having a wavelength $\lambda$, expressed in nm, other than 532.

2. The process according to claim 7, wherein said cosmetic hair treatment process comprises at least one process selected from the group consisting of permanent reshaping, dyeing, shampooing, conditioning, setting and lacquering.

3. The process according to claim 1, wherein said bleaching consists essentially of arranging hair in locks and irradiating said locks with laser radiation of sufficient power to bleach the hair.

4. The process according to claim 2, wherein said bleaching comprises arranging hair in locks and irradiating said locks with laser radiation of sufficient power to bleach the hair.

5. The process according to claim 1, wherein said cosmetic treatment further comprises permanent waving.

6. The process according to claim 1, wherein said cosmetic treatment further comprises hair dyeing.

7. The process according to claim 1, wherein said cosmetic treatment further comprises hair setting.

8. The process according to claim 1, wherein said cosmetic treatment further comprises hair shampooing.

9. In a cosmetic hair treatment process comprising bleaching said hair and at least one of permanent reshaping, dyeing, shampooing, conditioning, setting and lacquering said bleached hair, the improvement which comprises irradiating said hair with a laser beam to achieve said bleaching, said irradiating comprising delivering an energy density per pulse of 0.1 to 1.2 J/cm$^2$ for a wavelength of 532 nm, said energy density not being greater than that which degrades the keratinous fibers of said hair, wherein the energy density is multiplied by a correction factor equal to $\lambda/532$ for a radiation having a wavelength $\lambda$, expressed in nm, other than 532.

* * * * *